(12) United States Patent
Ashton et al.

(10) Patent No.: US 9,486,459 B2
(45) Date of Patent: *Nov. 8, 2016

(54) POROUS SILICON DRUG-ELUTING PARTICLES

(71) Applicant: pSivida US, Inc., Watertown, MA (US)

(72) Inventors: Paul Ashton, Newton, MA (US); Hong Guo, Wayland, MA (US); Jianbing Chen, Wayland, MA (US); Leigh T. Canham, Malvern (GB)

(73) Assignee: pSivida US, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/680,430

(22) Filed: Apr. 7, 2015

(65) Prior Publication Data

US 2015/0272965 A1   Oct. 1, 2015

Related U.S. Application Data

(63) Continuation of application No. 12/773,127, filed on May 4, 2010, now Pat. No. 9,023,896.

(60) Provisional application No. 61/175,379, filed on May 4, 2009.

(51) Int. Cl.
   *A61K 31/58* (2006.01)
   *A61K 9/00* (2006.01)

(52) U.S. Cl.
   CPC ............. *A61K 31/58* (2013.01); *A61K 9/0048* (2013.01); *A61K 9/0097* (2013.01)

(58) Field of Classification Search
   CPC .......................... A61K 9/0097; A61K 31/58
   See application file for complete search history.

(56) References Cited

U.S. PATENT DOCUMENTS 3,832,458 A    8/1974  Merrill
3,919,060 A    11/1975 Pogge et al.
(Continued)

FOREIGN PATENT DOCUMENTS

EP    0178769 A2    4/1986
EP    1776949 A2    4/2007
(Continued)

OTHER PUBLICATIONS

Amorij et al., "Development of stable influenza vaccine powder formulations challenges and possibilities." Pharmaceutical Research, 25(6):1261 (2008).
(Continued)

*Primary Examiner* — Michael B Pallay
(74) *Attorney, Agent, or Firm* — Foley Hoag LLP; David P. Halstead (57) ABSTRACT

The invention provides a biodegradable drug-eluting particle useful for the delivery of diagnostic or therapeutic agents. In certain embodiments, the drug-eluting particle of the invention comprises a biodegradable porous silicon body, a reservoir formed within the porous silicon body having at least one opening to an exterior of the body, wherein the reservoir contains a therapeutic or diagnostic agent, and an agent-permeable seal disposed over the at least one opening. The invention further provides a method for treating a patient to obtain a desired local or systemic physiological or pharmacological effect comprising administering a sustained release drug delivery particle of the invention. The invention also provides methods of fabricating a drug-eluting particle for releasing therapeutic agents.

34 Claims, 6 Drawing Sheets

(56) References Cited

U.S. PATENT DOCUMENTS

| | | | |
|---|---|---|---|
| 3,919,723 A | 11/1975 | Heimke et al. | |
| 4,036,979 A | 7/1977 | Asato | |
| 4,608,048 A | 8/1986 | Cortese et al. | |
| 4,772,203 A | 9/1988 | Scheunemann | |
| 4,793,825 A | 12/1988 | Benjamin et al. | |
| 5,057,082 A | 10/1991 | Burchette, Jr. | |
| 5,370,630 A | 12/1994 | Smidebush et al. | |
| 5,591,453 A | 1/1997 | Ducheyne et al. | |
| 5,665,114 A | 9/1997 | Weadock et al. | |
| 5,665,428 A | 9/1997 | Cha et al. | |
| 5,792,099 A | 8/1998 | DeCamp et al. | |
| 5,797,898 A | 8/1998 | Santini, Jr. et al. | |
| 5,807,574 A | 9/1998 | Cheskin et al. | |
| 5,874,109 A | 2/1999 | Ducheyne et al. | |
| 5,922,299 A | 7/1999 | Bruinsma et al. | |
| 6,060,036 A | 5/2000 | Armini | |
| 6,086,908 A | 7/2000 | Gopferich | |
| 6,238,705 B1 | 5/2001 | Liu et al. | |
| 6,322,895 B1 | 11/2001 | Canham | |
| 6,521,284 B1 | 2/2003 | Parsons et al. | |
| 6,666,214 B2 | 12/2003 | Canham | |
| 6,696,258 B1 | 2/2004 | Wei et al. | |
| 6,770,480 B1 | 8/2004 | Canham | |
| 6,929,950 B2 | 8/2005 | Canham et al. | |
| 7,090,681 B2 | 8/2006 | Weber et al. | |
| 7,332,339 B2 | 2/2008 | Canham | |
| 7,433,811 B2 | 10/2008 | Gao et al. | |
| 7,563,451 B2 | 7/2009 | Lin et al. | |
| 7,585,521 B2 | 9/2009 | Barbe et al. | |
| 7,713,778 B2 | 5/2010 | Li et al. | |
| 7,763,277 B1 | 7/2010 | Canham et al. | |
| 8,097,236 B2 | 1/2012 | Aston et al. | |
| 8,128,912 B2 | 3/2012 | Canham et al. | |
| 8,147,864 B2 | 4/2012 | Canham et al. | |
| 8,313,761 B2 | 11/2012 | Canham et al. | |
| 9,023,896 B2 * | 5/2015 | Ashton | A61K 9/0097 424/422 |
| 2002/0034646 A1 | 3/2002 | Canham | |
| 2004/0052867 A1 | 3/2004 | Canham | |
| 2004/0166140 A1 | 8/2004 | Santini et al. | |
| 2004/0170694 A1 | 9/2004 | Colic | |
| 2006/0067979 A1 * | 3/2006 | Kunzler | A61K 9/0051 424/427 |
| 2006/0154069 A1 | 7/2006 | Lin et al. | |
| 2006/0269893 A1 | 11/2006 | Aloise et al. | |
| 2007/0042046 A1 | 2/2007 | Saffie et al. | |
| 2007/0071787 A1 | 3/2007 | Saffie et al. | |
| 2008/0057101 A1 | 3/2008 | Roorda | |
| 2008/0241242 A1 | 10/2008 | Caruso et al. | |
| 2009/0137688 A1 | 5/2009 | Yang | |
| 2009/0208556 A1 | 8/2009 | Freeman et al. | |
| 2010/0278931 A1 | 11/2010 | Ashton et al. | |
| 2011/0052657 A1 | 3/2011 | Canham et al. | |
| 2011/0052653 A1 | 3/2011 | Canham et al. | |
| 2011/0182967 A1 | 7/2011 | Canham et al. | |
| 2011/0217353 A1 | 9/2011 | Canham et al. | |
| 2011/0217354 A1 | 9/2011 | Canham et al. | |
| 2011/0236493 A1 | 9/2011 | Canham et al. | |
| 2012/0177695 A1 | 7/2012 | Ashton et al. | |

FOREIGN PATENT DOCUMENTS

| | | | |
|---|---|---|---|
| JP | 59101145 | | 6/1984 |
| JP | 59131346 | | 7/1984 |
| JP | 10175994 A | | 6/1998 |
| JP | 2007091716 A | | 4/2007 |
| JP | 2010228986 A | | 10/2010 |
| WO | WO-90/11070 A1 | | 10/1990 |
| WO | WO-92/05777 A1 | | 4/1992 |
| WO | WO-94/21314 A1 | | 9/1994 |
| WO | WO-97/06101 A1 | | 2/1997 |
| WO | WO-97/32570 A1 | | 9/1997 |
| WO | WO-98/00107 A2 | | 1/1998 |
| WO | WO-99/39746 A2 | | 8/1999 |
| WO | WO-99/53898 A1 | | 10/1999 |
| WO | WO-00/05339 A1 | | 2/2000 |
| WO | WO-00/38655 A1 | | 7/2000 |
| WO | WO-01/28529 A1 | | 4/2001 |
| WO | WO-01/28587 A2 | | 4/2001 |
| WO | WO-01/32760 A1 | | 5/2001 |
| WO | WO-01/62232 A1 | | 8/2001 |
| WO | WO-01/62235 A2 | | 8/2001 |
| WO | WO-02/096389 A1 | | 12/2002 |
| WO | WO-2004/071949 A2 | | 8/2004 |
| WO | WO-2005/051358 A1 | | 6/2005 |
| WO | WO-2006/037160 A1 | | 4/2006 |
| WO | WO-2006/050221 A2 | | 5/2006 |
| WO | WO-2006/067979 A1 | | 6/2006 |
| WO | WO-2007/106868 A2 | | 9/2007 |
| WO | WO-2007/115261 A2 | | 10/2007 |
| WO | WO 2009009563 A2 * | 1/2009 | .......... A61K 9/0051 |
| WO | WO-2010/038068 A1 | | 4/2010 |
| WO | WO-2010/090596 A1 | | 8/2010 |
| WO | WO-2010/096733 A2 | | 8/2010 |
| WO | WO-2010/129545 A2 | | 11/2010 |
| WO | WO-2012/061377 A1 | | 5/2012 |
| WO | WO-2012/088306 A2 | | 6/2012 |

OTHER PUBLICATIONS

Anglin et al., "Porous Silicon in Drug Delivery Devices and Materials," Advanced Drug Delivery Reviews, 60:1266-1277 (2008).

Canham, "Porous Silicon as a Therapeutic Biomaterial," 1st Annual International IEEE-EMBS Special Topic Conference on Microtechnologies in medicine & Biology, Oct. 12-14, 2000, Lyon, France.

Cheng et al., "Intravitreal properties of porous silicon photonic crystals: a potential self-reporting intraocular drug delivery vehicle," Br. J. Ophthalmology, 92:705-711 (2008).

Cohen et al., "Microfabrication of Silicon-Based Nanoporous Particulates for Medical Applications," Biomedical Microdevices, 5(3):253-259 (2003).

International Preliminary Examination Report and Written Opinion dated May 7, 2013 for PCT/US2011/058774.

International Search Report dated Jan. 26, 2011, Serial No. PCT/US2010/033541.

Jarvis, K. et al., "Porous Silicon—A Nanostructured Delivery System," International Conference on Nanoscience and Nanotechnology,IEEE, 536-539 (2006).

Knott, M. "We have the technology . . . —The ultimate science-fiction wedding may be on early the next century when carbon life forms and silicon sensors get hitched," New Scientist, 51:2075, 36-39 (1997).

Kumar, D.S. et al., "Nanostructured Porous Silicon—A Novel Biomaterial for Drug Delivery," International Journal of Pharmacy and Pharmaceutical Sciences, 1(2):8-16 (2009).

Low, S. et al., "The biocompatibility of porous silicon in tissues of the eye," Biomaterials, 30:2873-2880 (2009).

Prestidge et al., "Mesoporous silicon: a platform for the delivery of therapeutics," Expert Opinion Drug Deliv., 4(2): 101-110 (2007).

Sinakten depo. "Suspenziya dlya vnutrimyshechnogo wedeniya 1mg/ml, ampula 1ml, 1-12 pachka kartonnaya 1, N2 P N013438/01," Sep. 30, 2005, Novartis Pharma, Nycomed Austria, [online], [retrieved on Jun. 26, 2014]. Retrieved from the internet <URL: http://www.rlsnet.ru/prep_index_id_59990.htm >, p. 1 (with machine translation).

Vadia et al., "Mesoporous material, MCM-41: A new drug carrier," Asian Journal of Pharmaceutical and Clinical Research, 4(2): 44-53 (2011).

Vinegoni et al., "Porous silicon microcavities," Silicon-Based Materials and Devices, 2:1-134 (2000).

Bourges, J.L. et al. "Intraocular Implants for Extended Drug Delivery: Therapeutic Applications" Advanced Drug Delivery Reviews 2006, 58, 1182-1202.

Haghjou, N. et al. "Sustained Release Intraocular Drug Delivery Devices for Treatment of Uveitis" Journal of Ophthalmic and Vision Research 2011; vol. 6, No. 4, pp. 317-329.

* cited by examiner

| | ID (Inches) | Area (mm²) | FA-RR (μg/day) | μg/mm² (day) |
|---|---|---|---|---|
| 1) PLLA | 0.011 | 0.1226 | 0.47 | 3.84 |
| 2) Polymide | 0.013 | 0.1712 | 0.64 | 3.75 |
| 3) Silicon | 0.019 (x9) | 1.645 | 6.5 | 3.95 |
| Ratio | | 2/1 = 1.40<br>3/1 = 13.8<br>3/2 = 9.6 | 2/1 = 1.36<br>3/1 = 13.4<br>3/2 = 10.1 | |

FIG. 8

POROUS SILICON DRUG-ELUTING PARTICLES

RELATED APPLICATIONS

This application is a continuation of U.S. patent application Ser. No. 12/773,127, filed May 4, 2010, which claims the benefit of priority to U.S. Provisional Application Ser. No. 61/175,379, filed May 4, 2009, each of which is hereby incorporated by reference in its entirety.

BACKGROUND OF THE INVENTION

The mode of administration and release kinetics of sustained-release drug formulations can have a profound effect on therapeutic efficacy. The use of polymer materials in this regard is well established and has led to numerous successful methods of both controlling drug release and providing sustained release over days to months, even years. Polymeric drug delivery devices for implantation in vivo have demonstrated durability and biocompatibility. Many of these drug delivery devices which provide sustained release of an agent, however, are inert under biological conditions resulting in the need for surgical resection following complete drug release.

An additional challenge is the difficulty in manufacturing materials with therapeutic agents and particularly maintaining uniformity among micron and sub-micron devices. Microfabrication techniques developed by the semiconductor industry have started to receive attention for developing timed pulsatile drug release systems such as presented in Santini et al. "Microchips as Controlled Drug Delivery Devices" *Angew. Chem. Int. Ed.* 39, 2396-2407, 2000, which is incorporated by reference herein.

There remains a need for biodegradable implantable drug delivery devices with controlled drug release that can be manufactured to consistent specifications on a micron or sub-micron scale.

SUMMARY OF THE INVENTION

One aspect of this invention provides a biodegradable drug-eluting particle useful for the delivery of diagnostic or therapeutic agents. In certain embodiments, the drug-eluting particle of the invention comprises a biodegradable porous silicon body, a reservoir formed within the porous silicon body having at least one opening to an exterior of the body, wherein the reservoir contains a drug core comprising a therapeutic or diagnostic agent, and an agent-permeable seal disposed over the at least one opening. In certain embodiments, the agent-permeable seal provides for sustained release of the agent. In particular embodiments, the particle is placed in vitro or in vivo.

The invention further provides a method for delivering an agent, e.g., via controlled and sustained administration, of a therapeutic or diagnostic agent to a patient, comprising inserting, injecting, or implanting a sustained-release drug-eluting particle of the invention at a desired location. Particles of the invention may be used in the treatment or prevention of diseases.

The invention also provides a method of fabricating a drug-eluting particle for releasing an agent comprising: providing a silicon wafer; depositing and patterning a material on the wafer for use as an etch mask; etching a plurality of reservoirs in the wafer; introducing pores into the silicon substrate; filling the reservoirs with a drug core comprising a therapeutic or diagnostic agent; and covering the reservoirs with a seal which is permeable to the agent.

DETAILED DESCRIPTION OF THE INVENTION

The present invention provides biodegradable drug-eluting particles for sustained release of a therapeutic or diagnostic agent ("the agent"). The particles are designed to release the agent in a controlled fashion and then biodegrade in the body, thereby avoiding the need for surgical resection of the particles. In certain embodiments, the drug-eluting particles of the invention are formed from silicon that is made biodegradable through porosification. Porous silicon is biocompatible and can be eroded in, or resorbed into, a patient without significant detrimental effect. In certain embodiments, the particle comprises a porous silicon body comprising a reservoir formed within the porous silicon body having at least one opening to an exterior of the body, wherein the reservoir contains a drug core comprising a therapeutic or diagnostic agent, and an agent-permeable seal disposed over the at least one opening. In certain embodiments, the seal provides for sustained release of the agent when the particle is administered to a patient. A patient, as used herein, refers to either a human or a non-human animal. Once the particle is administered to the patient, the agent diffuses through the permeable seal of the particle in a sustained fashion. The porous silicon body and agent-permeable seal that remain in the body after the useful life (e.g., therapeutic utility) of the particle has ended, erode under normal biological conditions to biocompatible byproducts. In other embodiments, the particles are used in an in vitro system.

Figure 1A:
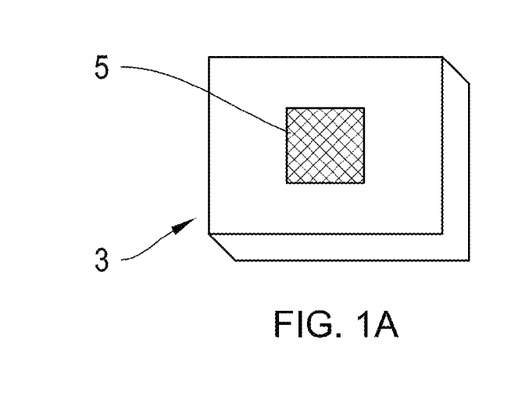
FIG. 1A-B consists of two panels, labeled "FIG. 1A" ("1A") and "FIG. 1B" ("1B"). Panel 1A depicts a top down view of a drug-eluting particle, and panel 1B depicts a cross-sectional view of a drug-eluting particle. The top down view (1A) depicts the porous silicon body 3 and the agent-permeable seal 5 disposed over the reservoir; the cross sectional side view (1B) depicts the porous silicon body 3, a reservoir 4 containing the therapeutic or diagnostic agent 6 and an agent-permeable seal 5.
Figure 1B:
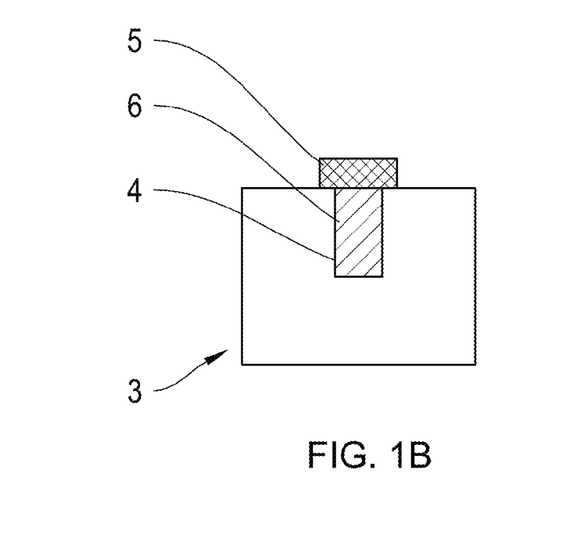
Figure 2:
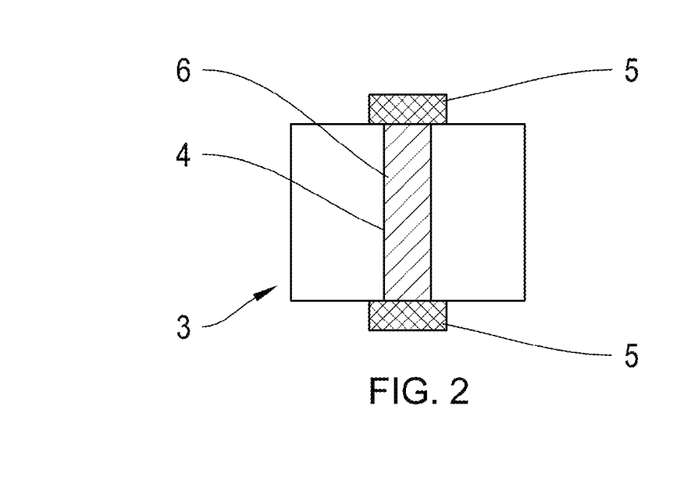
FIG. 2. A cross-sectional view of an alternative embodiment of the drug-eluting particle in which the reservoir 4 containing the agent 6 has two openings to the exterior of the porous silicon body 3, with an agent-permeable seal 5 disposed at each opening.
Figure 3:
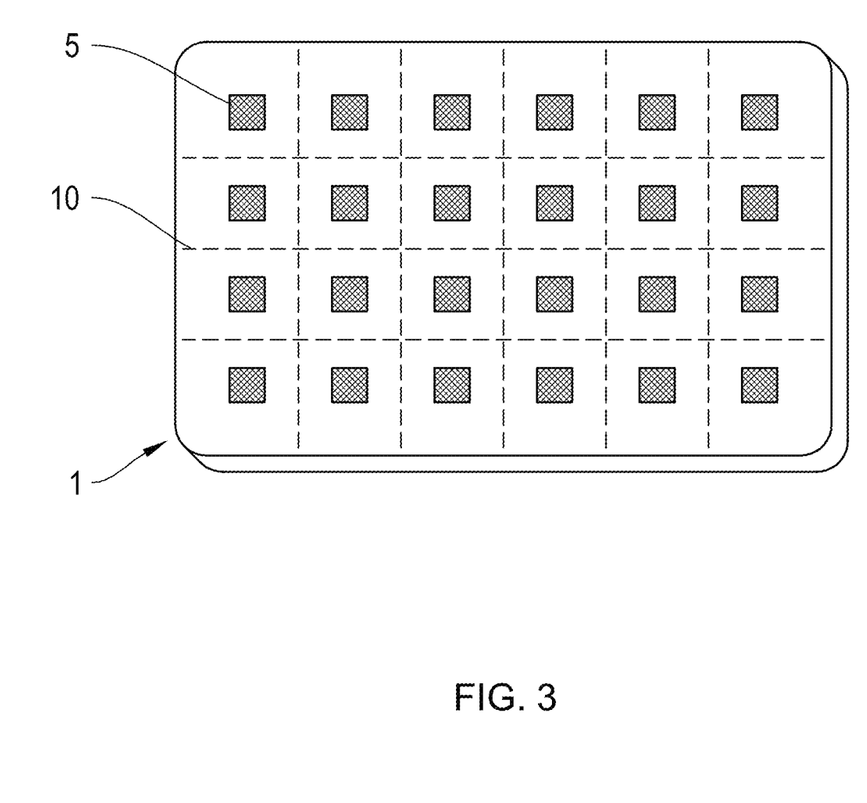
FIG. 3. Top down representation of array of drug-eluting particles prior to partitioning into individual drug-eluting particles.
Figure 4A:
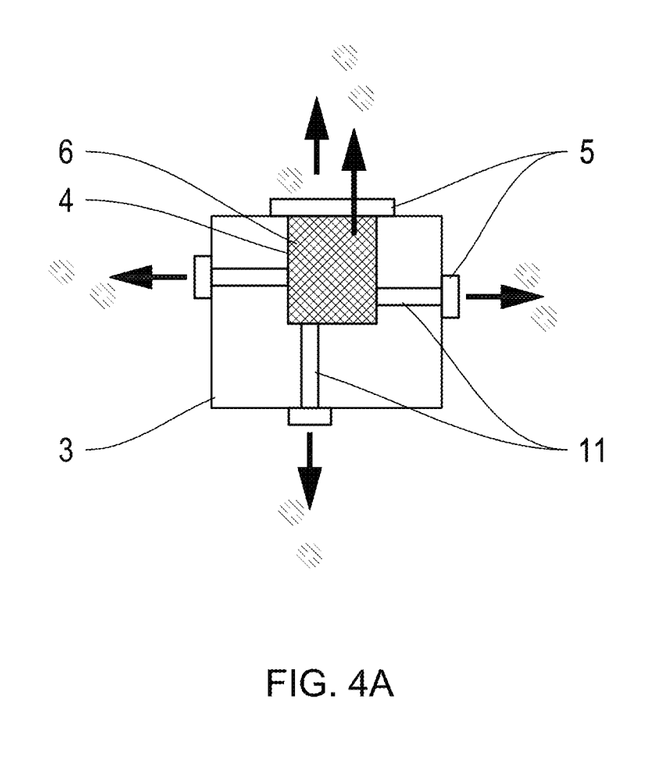
FIG. 4A-B consists of two panels, labeled "FIG. 4A" ("4A") and "FIG. 4B" ("4B"). Panels 4A and 4B depict cross-sectional views of a drug-eluting particle in which the particle comprises a porous silicon body 3, a reservoir 4 containing a therapeutic agent 6 wherein the reservoir has multiple openings 11 to an exterior of the body, and multiple agent-permeable seals 5 disposed over the openings (4A); or an agent-permeable membrane 12 disposed over the entire surface of the particle or over portions of the particle (4B). (Arrows represent the pathways of the agent's release from the reservoir.)
Figure 4B:
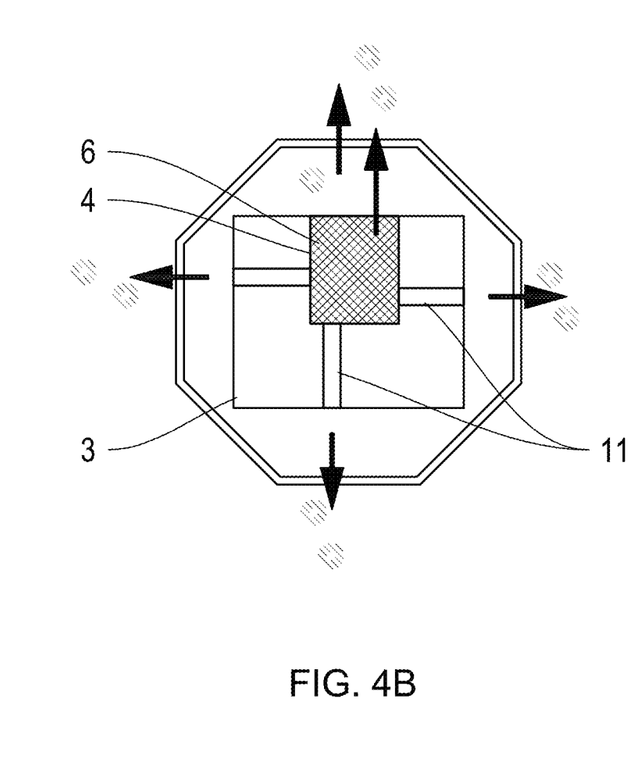

In certain embodiments, the drug-eluting particle comprises a porous silicon body 3, a reservoir 4 formed within the porous silicon body 3 having at least one opening to an exterior of the body, a drug core within the reservoir comprising a therapeutic or diagnostic agent 6, and an agent-permeable seal 5 disposed over the at least one opening (FIGS. 1a. top down view and b. side cross-sectional view). In certain embodiments, the seal provides for sustained release of the agent 6 when the particle is administered to a patient. In other embodiments, the reservoir 4 has at least two openings to an exterior of the body 3, and one or more agent-permeable seals 5 disposed over the at least two openings (FIG. 2). In other embodiments, the reservoir 4 has a plurality of openings 11 to an exterior of the body 3, and agent-permeable seals 5 disposed over the multiple openings (FIG. 4a). In certain embodiments, the seal is a membrane disposed over a portion of the surface, such as greater than 10%, greater than 15%, greater than 20%, greater than 30%, or greater than 40% of the surface of the porous silicon body, or the entirety of the surface of the particle. In an exemplary embodiment, a reservoir 4 has two or more openings 11 to an exterior of the body 3 and a permeable membrane 12 is disposed over the entirety of the surface of the particle (FIG. 4b). In certain embodiments, a permeable seal or a permeable membrane may be disposed over the at least one opening on the surface of the particle to regulate the release of the agent. In certain embodiments, the permeable seal or membrane is the only passage through which the agent is released from the particle in vivo or in vitro (e.g., prior to degradation of the particle itself).

In certain embodiments, the particle comprises more than one reservoir such as 2, 3, 4 or 5 reservoirs. In certain embodiments, each reservoir has at least one opening to the exterior of the body, with an agent-permeable seal or membrane disposed over the at least one opening. In certain embodiments, each reservoir has 2 or more openings and an agent permeable seal or membrane disposed over the at least 2 openings.

In certain embodiments, the drug-eluting particle of the invention is administered to a patient, e.g., by injection, for treating or preventing disease. The terms treating or treatment are intended to encompass prophylaxis and amelioration of symptoms, as well as therapy and cure. The term preventing is art-recognized, and when used in relation to a condition such as a local reoccurrence (e.g., pain), a disease such as cancer, a syndrome complex such as heart failure or any other medical condition, is well understood in the art and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes for example, reducing the number of diagnoses of the infection in a treated population versus an untreated control population, and/or delaying the onset of symptoms of the infection in a treated population versus and untreated control population. Prevention of pain includes, for example, reducing the magnitude of, or alternatively delaying, pain sensations experienced by subjects in a treated population versus an untreated control population.

In certain embodiments, the particle releases the agent in a sustained manner, e.g., such as over a period of hours, days, weeks, months or years. In certain embodiments, the particles biodegrade when the complete useful life of the particle has ended, such as days, weeks, months or years following administration.

The particles of the invention may possess any geometric form, such as a cube, a disc, a cylinder, a rectangular box, a pyramid, or any other regular or irregular shape. In certain embodiments, the particle is formed by subdividing, e.g., by controlled partitioning, a silicon wafer, e.g., such as are used in the electronics industry. In certain embodiments, the particle has a first and second side corresponding to the two planar faces of a silicon wafer. In particular embodiments, one planar face of the wafer is etched to form the reservoirs in the particle prior to the controlled fracture. It should be recognized that the two sides of the particle may be disposed in any orientation, e.g., substantially parallel or skew, and may have any suitable shape, e.g., concave, convex or planar.

In certain embodiments, the particles have at least one dimension less than 1 mm such as a dimension from 20-600 microns such as from 100-500 microns. In certain embodiments, the particles may be sufficiently small to be administered by injection through a needle such as a 21 gauge, a 22 gauge, a 23 gauge, a 24 gauge, a 25 gauge, a 26 gauge, a 27 gauge, a 28 gauge, or a 29 gauge needle. In particular embodiments, the particles are administered through a 25 gauge needle. The patient may be administered a single particle or multiple particles in a single administration. In certain embodiments, the patient is administered dozens or hundreds of particles.

In certain aspects, the present invention provides biodegradable silicon structures and their methods of manufacture for use as drug-eluting particles. Porous silicon structures, unlike crystalline silicon structures, have been shown to biodegrade in vitro and in vivo producing innocuous byproducts, i.e., monomeric silicic acid ($Si(OH)_4$). Silicic acid, which is naturally present in blood plasma at levels of less than 1 mg Si/L from the dietary intake of 20-50 mg/day, is readily removed by the kidneys. The rate of dissolution in biological media varies based on the pore size in the silicon. Very small pores (e.g., nm-μm diameters) can be introduced into crystalline silicon with a relatively high degree of uniformity and control using conventional integrated circuit and micromachining processing. Also, the high surface area pores of porous silicon can be coated with specific materials by existing silicon processing technology for the adsorption/desorption of liquids or gasses. In addition, the porous silicon can be fabricated as thin membranes, e.g., 50 μm thick, which can be bonded to other materials, such as Pyrex or glass. Some devices comprising porous silicon may be seen in U.S. Pat. No. 6,770,480, the contents of which are incorporated by reference herein.

Biodegradation, as used herein, refers to the chemical breakdown of materials by a physiological environment. The physiological environment under which the biodegradation occurs may be within an organism or external to an organism such as in a test tube or petri dish. Biocompatibility, as used herein, is related to the behavior of biomaterials in various contexts. The term may refer to specific properties of a material without specifying where or how the material is used (for example, that it elicits little or no immune response in a given organism, or is able to integrate with a particular cell type or tissue), or to more empirical clinical success of a whole particle in which the material or materials feature. The term biocompatible, as used herein, does not necessarily indicate that the material is biologically acceptable for all applications but merely that the material is biologically acceptable for a specific application of interest.

Porous silicon is commonly divided into three categories based on the size of its pores: macroporous, mesoporous and microporous. Macroporous silicon has a pore diameter larger than 50 nm, mesoporous silicon has a pore diameter between 2 and 50 nm, while microporous silicon has a pore diameter less than 2 nm. The pore size of the porous silicon affects the rate of biodegradation of the silicon; accordingly, the pore size may be selected on the basis of the intended lifespan of the particle. In certain embodiments, particles of the invention comprise mesoporous silicon, macroporous silicon, microporous silicon or a combination thereof. In certain embodiments, the particles comprise mesoporous silica.

In certain embodiments, the porous silicon of the present particle is essentially impermeable to the passage of the therapeutic or diagnostic agent. The term impermeable, as used herein, means that the layer will not allow passage of the agent at a rate sufficient to provide the desired local or systemic physiological or pharmacological effect. In other embodiments, the porous silicon body is coated with an agent-impermeable coating to prevent passage of the agent through the porous silicon. Such an agent-impermeable coating may be applied to the porous silicon body prior to the introduction of the drug core into the reservoir. In certain embodiments, the agent-impermeable coating is biodegradable.

In certain embodiments, the porous silicon body has a porosity from 4% to 90%. In certain embodiments, the body has a porosity from 20% to 70% such as a porosity from 30% to 60% such as a porosity of about 30% or of about 35% or of about 40% or of about 45% or of about 50% or of about 55% or of about 60%. Porosity, as used herein, is a measure of the void spaces in a material, and is measured as a fraction, between 0 and 1, or as a percentage between 0 and 100%.

In certain embodiments, the particles have applicability in providing a controlled and sustained release of agents effective in obtaining a desired local or systemic physiological or pharmacological effect for treating or preventing: cancer, such as cancerous primary tumors (e.g., glioblastoma); neovascularization, including ocular neovascularization; edema, including ocular edema; inflammation, including ocular inflammation; chronic pain; arthritis; rheumatic conditions; hormonal deficiencies such as diabetes and dwarfism; or immune responses such as transplant rejection. A wide variety of other disease states may also be prevented or treated using the drug delivery particle of the present invention. Such disease states are known by those of ordinary skill in the art. Reference may be made to Goodman and Gilman, *The Pharmacological Basis of Therapeutics*, 8th Edition, Pergamon Press, NY, 1990; and *Remington's Pharmaceutical Sciences*, 18th Edition, Mack Publishing Co., Easton, Pa., 1990; both of which are incorporated by reference herein.

In addition, the particles are suitable for use in treating mammalian organisms infected with HIV and AIDS-related opportunistic infections such as cytomegalovirus infections, toxoplasmosis, pneumocystis carinii, and mycobacterium avium intercellular.

The particles are particularly suitable for treating or preventing an ocular condition such as glaucoma, proliferative vitreoretinopathy, macular edema, including diabetic macular edema, age-related macular degeneration, diabetic retinopathy, uveitis, ocular neovascularization, and ocular infection. The particles are also particularly suitable for treating mammalian organisms, both human and for veterinarian use, suffering from ocular histoplasmosis, e.g., wherein the particle is inserted or injected into the vitreous of the eye.

As described above, in certain embodiments, the drug core comprises a therapeutic agent effective in obtaining a desired local or systemic physiological or pharmacological effect. The following classes of agents could be incorporated into the drug core of the particles of the present invention: anesthetics and pain killing agents such as lidocaine and related compounds and benzodiazepam and related compounds; anti-cancer agents such as 5-fluorouracil, adriamycin and related compounds; anti-inflammatory agents such as 6-mannose phosphate; anti-fungal agents such as fluconazole and related compounds; anti-viral agents such as trisodium phosphomonoformate, trifluorothymidine, acyclovir, ganciclovir, DDI, DDC, and AZT; cell transport/mobility impending agents such as colchicine, vincristine, cytochalasin B, and related compounds; antiglaucoma drugs such as beta-blockers: timolol, betaxol, atenalol, etc; immunological response modifiers such as muramyl dipeptide and related compounds; peptides and proteins such as cyclosporin, insulin, growth hormones, insulin related growth factor, heat shock proteins and related compounds; steroidal compounds such as dexamethasone, prednisolone and related compounds; corticosteroids such as fluocinolone acetonide and related compounds; and carbonic anhydrase inhibitors. The phrases systemic administration and administered systemically, as used herein, mean the administration of a compound, drug or other material other than directly into the central nervous system, such that it enters the patient's system and, thus, is subject to metabolism and other like processes, for example, subcutaneous administration. Local administration refers to administration at the site where the target cells are present, i.e., in a specific tissue, organ, or fluid (e.g., blood, cerebrospinal fluid, etc.).

In addition to the above agents, other agents are suitable for administration to the eye and its surrounding tissues to produce a local or a systemic physiologic or pharmacologic beneficial effect. Examples of such agents include neuroprotectants such as nimodipine and related compounds; antibiotics such as tetracycline, chlortetracycline, bacitracin, neomycin, polyrnyxin, gramicidin, oxytetracycline, chloramphenicol, gentamycin, and erythromycin; antibacterials such as sulfonamides, sulfacetamide, sulfamethizole and, sulfisoxazole; antivirals, including idoxuridine; and other antibacterial agents such as nitrofurazone and sodium propionate; antiallergenics such as antazoline, methapyriline, chlorpheniramine, pyrilamine, and prophenpyridamine; anti-inflammatories such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone, and triminolone; decongestants such as phenylephrine, naphazoline, and tetrahydrazoline; miotics and anti-cholinesterase such as pilocarpine, eserine salicylate, carbachol, di-isopropyl fluorophosphate, phospholine iodine, and demecarium bromide; mydriatics such as atropine sulfate, cyclopentolate, homatropine, scopolamine, tropicamide, eucatropine, and hydroxyamphetamine; sympathomimetics such as epinephrine; and prodrugs such as those described in Design of Prodrugs, edited by Hans Bundgaard, Elsevier Scientific Publishing Co., Amsterdam, 1985. Once again, reference may be made to any standard pharmaceutical textbook such as Remington's Pharmaceutical Sciences for the identity of other agents.

In certain embodiments, particles of the invention comprise a diagnostic agent. Exemplary diagnostic agents for ophthalmic use include sodium fluorescein, rose bengal, methacholine, adrenaline, cocaine, and atropine. In certain embodiments, the particles of the invention comprise a surgical additive. Exemplary surgical additives for ophthalmic use include alpha-chymotrypsin and hyaluronidase.

Any pharmaceutically acceptable form of any diagnostic or therapeutic agent may be employed in the practice of the present invention, e.g., a free base or free acid or a pharmaceutically acceptable salt or ester thereof. Pharmaceutically acceptable salts, for instance, include sulfate, lactate, acetate, stearate, hydrochloride, tartrate, maleate, and the like.

In certain embodiments, drug core of the drug-eluting particles of the invention comprise from 0.01 mg to 50 mg of the agent. For example, in certain embodiments, the drug-eluting particles comprise from 0.01 mg to 40 mg of the agent, such as from 0.05 mg to 20 mg of the agent. In certain embodiments, particle comprises a single reservoir which contains from 0.01 to 5 mg of the agent such as from 0.05 to 2 mg, such as from 0.1 to 1 mg of the agent. In certain embodiments, the particle comprises more than one reservoir wherein each reservoir contains from 0.5 to 10 mg of the agent.

In addition to a therapeutic agent, the drug reservoir may include additional components such as pharmaceutically acceptable carriers or an additional therapeutic agent. In certain embodiments, the reservoir comprises a therapeutic agent and a biocompatible polymer, such as polyvinyl alcohol (PVA), forming a drug core. Biocompatible polymers are known in the art and exemplary polymers are presented herein. Such a drug core may serve to rigidify a drug solution, thus setting an otherwise liquid drug as a solid or semi-solid within the reservoir. The drug core may also serve to delay release of the therapeutic agent from the particle. Pharmaceutically acceptable carriers may be added to the therapeutic agent for a variety of reasons such as ease of manufacturing, stabilizing the therapeutic agent, and altering the viscosity for loading into the particles. In certain embodiments, the drug core comprises the agent, a polymer and one or more carriers. In certain embodiments, the drug core comprises one or more agents. In certain embodiments, the drug core comprises one or more polymeric agents such a cross-linked polymers or cross-linked gelatins.

The term pharmaceutically acceptable carrier is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

In addition to the porous silicon of the particle, additional naturally occurring or synthetic materials that are biologically compatible with body fluids and eye tissues may be used in manufacturing the particles of the invention. For example, materials compatible with body fluids with which the particles will come in contact include, but are not limited to: ethyl vinyl acetate, polyvinyl acetate, cross-linked polyvinyl alcohol, cross-linked polyvinyl butyrate, ethylene ethylacrylate copolymer, polyethyl hexylacrylate, polyvinyl chloride, polyvinyl acetals, plasticized ethylene vinylacetate copolymer, polyvinyl alcohol, polyvinyl acetate, ethylene vinylchloride copolymer, polyvinyl esters, polyvinylbutyrate, polyvinylformal, polyamides, polymethylmethacrylate, polybutylmethacrylate, plasticized polyvinyl chloride, plasticized nylon, plasticized soft nylon, plasticized polyethylene terephthalate, natural rubber, polyisoprene, polyisobutylene, polybutadiene, polyethylene, polytetrafluoroethylene, polyvinylidene chloride, polyacrylonitrile, cross-linked polyvinylpyrrolidone, polytrifluorochloroethylene, chlorinated polyethylene, poly(1,4'-isopropylidene diphenylene carbonate), vinylidene chloride, acrylonitrile copolymer, vinyl chloride-diethyl fumarate copolymer, silicone rubbers, especially the medical grade polydimethylsiloxanes, ethylene-propylene rubber, silicone-carbonate copolymers, vinylidene chloride-vinyl chloride copolymer, vinyl chloride-acrylonitrile copolymer, vinylidene chloride-acrylonitride copolymer, gold, platinum, and (surgical) stainless steel.

In certain embodiments, the composition of the agent-permeable seal or agent-permeable membrane is selected so as to allow the above-described controlled release. In certain embodiments, the agent-permeable membrane of the invention is a seal that covers one or more openings of the porous silicon body and, in addition, covers surface area beyond the opening. For example, the membrane may cover an entire side or two sides of the particle, extending beyond the opening of the reservoir. In certain embodiments, the membrane covers multiple openings such as 2, 3 or 4 openings, In certain embodiments, the reservoir covers a percentage of the surface area of the particle including the surface of the openings such as at least about 10% of the surface, at least about 20% of the surface, at least about 30%, of the surface, at least about 40% of the surface, at least about 50% of the surface, at least about 60% of the surface or even at least about 70% of the surface, such as from 10-90% of the surface or 10-70% of the surface. In such embodiments, the membrane, similar to the seal, serves to control the release of the agent from the particle. The preferred composition of the agent-permeable seal or membrane will vary depending on such factors as the agent, the desired rate of release, and the mode of administration. The identity of the agent may also be a factor in the rate of release, since the size of the molecule, its solubility, and its polarity may play a role in determining the rate of release of the agent. In certain embodiments, the agent-permeable seal or membrane is impermeable to components in a biological environment such as proteins, nucleic acids, carbohydrates, lipids, cells or cellular components.

The agent diffuses in the direction of lower chemical potential, i.e., toward the exterior surface of the particle. At the exterior surface of the particle, equilibrium is again established. When the conditions on both sides of the seal or membrane are maintained constant, a steady state flux of the effective agent will be established in accordance with Fick's Law of Diffusion. The rate of passage of the drug through the material by diffusion is generally dependent on the solubility of the drug therein, as well as on the thickness of the seal or membrane. This means that selection of appropriate materials for fabricating the seal or membrane will be dependent on the particular drug to be used. Sustained drug delivery devices that utilize diffusion include those disclosed in U.S. Pat. No. 6,375,972 which is incorporated by reference herein.

The rate of diffusion of the therapeutic agent through a agent-permeable seal or membrane of the present invention may be determined via diffusion cell studies carried out under sink conditions. In diffusion cell studies carried out under sink conditions, the concentration of drug in the receptor compartment is essentially zero when compared to the high concentration in the donor compartment. Under these conditions, the rate of drug release is given by:

$$Q/t = (D \cdot K \cdot A \cdot DC)/h$$

where Q is the amount of drug released, t is time, D is the diffusion coefficient, K is the partition coefficient, A is the surface area, DC is the difference in concentration of the drug across the membrane, and h is the thickness of the membrane.

In the case where the agent diffuses through the layer via water filled pores, there is no partitioning phenomena. Thus, K can be eliminated from the equation. Under sink conditions, if release from the donor side is very slow, the value of DC is essentially constant and equal to the concentration of the donor compartment. Release rate therefore becomes dependent on the surface area (A), thickness (h), and diffusivity (D) of the membrane. In the construction of the particles of the present invention, the size (and therefore, surface area) is mainly dependent on the size of the effective agent.

Thus, permeability values may be obtained from the slopes of a Q versus time plot. The permeability P, can be related to the diffusion coefficient D, by:

$$P = (K \cdot D)/h$$

Exemplary permeable materials suitable for use as seals or membranes, are described in U.S. Pat. No. 4,014,335, which is incorporated herein by reference in its entirety. These materials include, but are not limited to: cross-linked polyvinyl alcohol, polyolefins or polyvinyl chlorides or cross-linked gelatins; regenerated, insoluble, non-erodible cellulose, acylated cellulose, esterified celluloses, cellulose acetate propionate, cellulose acetate butyrate, cellulose acetate phthalate, cellulose acetate diethyl-aminoacetate; polyurethanes, polycarbonates, and microporous polymers formed by co-precipitation of a polycation and a polyanion modified insoluble collagen. In certain embodiments, the reservoir seal is formed from one or more cross-linked polymers such as cross-linked polyvinyl alcohol.

The body of the particle may be modified with agents that enhance biocompatibility or target the particle to a specific location. For example, the surface of the silicon may be coated with a biocompatibility agent, e.g., apatite, to improve biocompatiblity. Other exemplary silicon modifications suitable for use with the particles disclosed herein are described in U.S. Pat. No. 6,666,214 incorporated herein by reference in its entirety.

In certain embodiments, the body of the particle comprises a targeting moiety. In certain embodiments, one or more targeting moieties are bound to the surface of the particle through covalent or non-covalent forces. The targeting moiety, which assists the particle in localizing to a particular target area, may be selected on the basis of the particular condition or site to be monitored. The targeting moiety may further comprise any of a number of different chemical entities. In one embodiment, the targeting moiety is a small molecule. Molecules which may be suitable for use as targeting moieties in the present invention include haptens, epitopes, and dsDNA fragments and analogs and derivatives thereof. Such moieties bind specifically to antibodies, fragments or analogs thereof, including mimetics (for haptens and epitopes), and zinc finger proteins (for dsDNA fragments). Nutrients believed to trigger receptor-mediated endocytosis and therefore useful targeting moieties include biotin, folate, riboflavin, carnitine, inositol, lipoic acid, niacin, pantothenic acid, thiamin, pyridoxal, ascorbic acid, and the lipid soluble vitamins A, D, E and K. Another exemplary type of small molecule targeting moiety includes steroidal lipids, such as cholesterol, and steroidal hormones, such as estradiol, testosterone, etc.

In another embodiment, the targeting moiety may comprise a protein. Particular types of proteins may be selected based on known characteristics of the target site or target cells. For example, the probe can be an antibody either monoclonal or polyclonal, where a corresponding antigen is displayed at the target site. In situations wherein a certain receptor is expressed by the target cells, the targeting moiety may comprise a protein or peptidomimetic ligand capable of binding to that receptor. Protein ligands of known cell surface receptors include low density lipoproteins, transferrin, insulin, fibrinolytic enzymes, anti-HER2, platelet binding proteins such as annexins, and biological response modifiers (including interleukin, interferon, erythropoietin and colony-stimulating factor). A number of monoclonal antibodies that bind to a specific type of cell have been developed, including monoclonal antibodies specific for tumor-associated antigens in humans. Among the many such monoclonal antibodies that may be used are anti-TAC, or other interleukin-2receptor antibodies; 9.2.27 and NR-ML-05 to the 250 kilodalton human melanoma-associated proteoglycan; and NR-LU-10 to a pancarcinoma glycoprotein. An antibody employed in the present invention may be an intact (whole) molecule, a fragment thereof, or a functional equivalent thereof. Examples of antibody fragments are $F(ab')_2$, Fab', Fab, and $F_v$ fragments, which may be produced by conventional methods or by genetic or protein engineering.

Other preferred targeting moieties include sugars (e.g., glucose, fucose, galactose, mannose) that are recognized by target-specific receptors. For example, drug-eluting particles can be modified with mannose residues (e.g., attached as C-glycosides to a free nitrogen) to yield targeted particles having higher affinity binding to tumors expressing mannose receptors (e.g., glioblastomas and gangliocytomas), and bacteria, which are also known to express mannose receptors (Bertozzi, C R and M D Bednarski Carbohydrate Research 223:243 (1992); J. Am. Chem. Soc. 114:2242, 5543 (1992)), as well as potentially other infectious agents. Certain cells, such as malignant cells and blood cells (e.g., A, AB, B, etc.)

display particular carbohydrates, for which a corresponding lectin may serve as a targeting moiety.

In certain embodiments, the particles are partially or completely biodegradable in a patient. For example, the particle may comprise biodegradable polymers, porous silicon and a therapeutic agent, such that after the useful life of the particle, the particle completely degrades to innocuous by-products. In other exemplary embodiments, the particle may include materials that are biodegradable and non-biodegradable. In such embodiments, the non-biodegradable component may need to be removed from the body following drug release.

In certain embodiments, the particles have a lifespan of hours, days, weeks, months or years. The term lifespan, as defined herein, refers to the time between a particle's introduction into a biological environment, e.g., in vivo or in vitro, until the particle has completely biodegraded. In exemplary embodiments, the particle may completely degrade within hours or days such as from 4 to 24 hours, such as about 5 hours, about 10 hours, about 15 hours, about 20 hours, about 1 day, or from 2 days to 2 weeks, such as about 2 days about 5 days, about 10 days, or greater than 2 weeks, such as about 15 days, or about 20 days. In certain embodiments, the particles degrade over a period of weeks or months such as about 3 weeks, about 1 month, about 2 months, about 3 months, about 6 months, about 9 months, about 1 year, about 2 years or about 3 years.

The invention also provides methods of fabricating a drug-eluting particle for releasing an agent comprising: providing a silicon wafer; depositing and patterning a material on the wafer for use as an etch mask; etching a plurality of reservoirs in the wafer; introducing pores into the silicon substrate; filling the reservoirs with a drug core comprising a therapeutic or diagnostic agent; and covering the reservoirs with a seal which is permeable to the agent. In certain embodiments, the method further comprises a controlled partitioning of the wafer into a number of discrete particles, e.g., each comprising one reservoir.

Methods of the invention include methods of manufacturing porous silicon particles for sustained drug release. In exemplary embodiments, such processes may begin by modifying bulk silicon wafers, such as electronics-grade silicon, by standard methods known in the art of silicon microfabrication and microelectromechanical systems (MEMS) in particular. In an exemplary embodiment, silicon wafers with diameters in the range of 75-350 mm in diameter and 0.05-2.0 mm in thickness may be used for producing arrays of particles. In particular embodiments, the wafers are 150 mm, 200 mm or 300 mm in diameter. In certain embodiments, the wafers are heavily p-type wafers with resistivity in the range of 0.1-0.001 ohm cm.

In certain embodiments, silicon wafers are etched on one face of the wafer to generate reservoirs as described above. This may be accomplished by patterning the wafer with a mask for creating arrays of reservoirs followed by etching by any method suitable for etching silicon, e.g., wet or dry etching. Photolithography, which uses light to transfer a geometric pattern from a photomask to a light-sensitive chemical (photoresist, or simply "resist") on the wafer, may be used to pattern the wafer. The exposure pattern from photolithography is engraved into the material under the photoresist with chemical treatments. In certain embodiments, the process creates reservoirs in the silicon wafer which are roughly cylindrical and have diameters of about 300 μm to about 120 μm such as about 320 μm, about 300 μm, about 280 μm, about 260 μm, about 250 μm, about 240 μm, about 220 μm, about 200 μm, about 180 μm, about 160 μm, or about 140 μm. In certain embodiments, the reservoirs have depths of about 500 μm to about 1 mm such as about 500 μm, about 525 μm, About 550 μm, about 575 μm, about 600 μm, about 625 μm, about 650 μm, about 675 μm, about 700 μm, about 725 μm, about 750 μm, about 775 μm, about 800 μm, about 825 μm, about 850 μm, about 875 μm, or about 900 μm. The reservoirs may take the form of any geometric or amorphous shape such as a cylinder, a rectangular box, a pyramid, or an amorphous shaped reservoir. The diameter for non-cylindrical reservoirs refers to the largest width measurement of a reservoir.

In certain embodiments, the etched silicon wafer is porosified by any method in the art known for porosifying silicon. In certain embodiments, silicon wafers may be porosified through an anodization cell. In an exemplary embodiment, a platinum cathode and silicon wafer anode are immersed in Hydrogen Fluoride (HF) electrolyte. Corrosion of the anode is produced by running electrical current through the cell. In certain embodiments, DC current is implemented. In certain embodiments, the silicon wafer may be porosified through stain-etching with hydrofluoric acid, nitric acid and water. The porosity of the silicon can be increased during processing through increasing current density, decreasing HF concentration and employing a thicker silicon layer. In certain embodiments, etching a plurality of reservoirs in the wafer is performed prior to, e.g., immediately prior to or a step or more prior in the process, introducing pores into the silicon body. In certain alternative embodiments, introducing pores into the silicon wafer is performed prior to, e.g., immediately prior to or a step or more prior in the process, etching a plurality of reservoirs in the wafer.

The surface of the etched porous silicon wafers may be modified to exhibit desired characteristics. The surface may be oxidized through a controlled oxidation step such as by thermal oxidation or chemical oxidizing agents. In certain embodiments, the etched porous wafer is covered with a coating that is impermeable to the agent. In such embodiments, the covering of the etched porous wafer with an agent-impermeable coating is performed prior to, e.g., immediately prior to or a step or more prior in the process, the filling of the reservoirs with the drug core. In certain such embodiments, the membrane is a biodegradable polymer.

In certain embodiments, the reservoirs of the porous silicon wafer may be filled with a drug core comprising a therapeutic or diagnostic agent by methods known in the art of micromachining. Methods for filling reservoirs include, but are not limited to, methods that exploit capillary forces such as solvent techniques or ink jet printing and microinjection techniques. In other embodiments, an array of microinjectors is designed and aligned to match the reservoir array and insure massive parallel injection from each nozzle to a micromachined reservoir.

The filled reservoirs may then be covered with an agent-permeable seal, e.g., multiple individual seals wherein one discrete seal is disposed on each opening, a permeable seal wherein one seal covers plurality of openings, or a membrane, wherein the membrane covers a portion or the entirety of the surface of the particle. In certain embodiments, the opening of the reservoir is covered with a agent-permeable membrane which covers a portion of the surface of the porous silicon body, such as greater than 10%, greater than 15%, greater than 20%, greater than 30% or greater than 40% of the surface of the porous silicon body. In certain embodiments, the filled reservoirs may be covered by any method known in the art, e.g., standard techniques for depositing polymeric materials. Methods for depositing thin films of material with a thickness of anywhere from a few nanometers to about 100 micrometers include, but are not limited to, spray coating, dipping, electroplating, sputter deposition, physical vapour deposition (PVD) and chemical vapour deposition (CVD). In certain embodiments, the permeable seal comprises one or more polymers.

The reservoir array, e.g., wafer, may be subdivided, e.g., through a controlled partitioning, into a number of discrete particles, e.g., each comprising one reservoir. To facilitate this separation, the micromachining process may be modified to include formation of one or more shallow trenches between reservoirs of the array, or otherwise scoring the surface of the array to define individual particles of the invention. The controlled partitioning of the array may then be induced along the shallow trenches. The reservoir array may also be cut into pieces using a high precision dicing machine. Using either of the mentioned methods or any other suitable method for subdividing the array into individual particles, it will be appreciated that the resulting individual particles may each have one or more reservoirs. In certain embodiments, the reservoir array is fractured into discrete particles, each of which contains the same number of reservoirs such as a single reservoir, 2 reservoirs, 3 reservoirs, 4 reservoirs, 5 reservoirs, 6 reservoirs, 7 reservoirs, 8 reservoirs, 9 reservoirs, or 10 reservoirs. In other embodiments, the array is fractured into discrete particles in which each particle has from 1-10 reservoirs. In particles which include more than one reservoir, different reservoirs of a particle may include different drug cores releasing different therapeutic or diagnostic agents, or each reservoir may include the same therapeutic or diagnostic agent for diffusion out of the particle.

The above description of how to make the particles of the present invention is merely illustrative and should not be considered as limiting the scope of the invention in any way, as various compositions are well known by those skilled in the art. In particular, the methods of making the particle may be varied to account for the identity of the therapeutic agent, porous silicon characteristics and polymers selected. The order of the steps of the process may be interchanged as appropriate to obtain the particles of the invention.

Methods of the invention include the administration of particles of the invention to a patient. In certain embodiments, the invention provides a method for delivering an agent, e.g., via controlled and sustained administration, of a therapeutic or diagnostic agent to a patient. The term administering, as used herein, means positioning, inserting, injecting, implanting or any other means for exposing the particle to a patient. The route of administration may be selected based on a variety of factors including effective amount and physical phase of the agent, type of agent and preferred site of administration. The method for treating a patient, e.g., mammalian organism, to obtain a desired local or systemic physiological or pharmacological effect comprises administering the sustained-release drug delivery particle of the present invention to the patient and allowing the agent to elute from the particle and come in direct contact with cells or tissues of the patient.

The drug delivery particle of the present invention may be administered to a patient via any route of administration known in the art. Such routes of administration include intraocular, oral, subcutaneous, intramuscular, intraperitoneal, intranasal, dermal, into the brain, including intracranial and intradural, into the joints, including ankles, knees, hips, shoulders, elbows, wrists, directly into tumors, and the like. In certain embodiments, one or more of the particles may be administered at one time, such as 2 or more particles, dozens of particles, or hundreds of particles.

The drug delivery system of the present invention is particularly suitable for direct implantation into the vitreous of the eye and for application to an intraocular lens.

For localized drug delivery, the particles may be inserted at or near the site of action such as via syringe or surgical implantation. In certain embodiments, the particles of the present invention are used for localized drug delivery in treating ocular conditions, primary tumors, rheumatic and arthritic conditions, and chronic pain.

For systemic relief, the particles may be implanted subcutaneously, intramuscularly, intraarterially, intrathecally, or intraperitoneally. In certain embodiments, the particles of the present invention are used to provide sustained systemic levels and avoid premature metabolism. In addition, such particles may be administered orally.

In certain embodiments the therapeutic agent is released from the particles of the invention over the course of hours or days. In certain embodiments, the therapeutic agent is released from the particle over the course of at least about one hour, about 2 hours, about 3 hours, about 5 hours, about 10 hours, about 15 hours, about 20 hours, about 1 day, about 2 days about 5 days, about 10 days, about 15 days, or at least about 20 days. In certain embodiments, the agent is released over the course of weeks, months or years such as about 1 week, about 2 weeks, about 4 weeks, about 6 weeks, about 8 weeks, about 3 months, about 4 months, about 6 months about 9 months or about 1 year.

In one embodiment of the invention, an ocular particle containing fluocinolone acetonide as the effective agent in a therapeutically effective amount to reduce or prevent ocular neovascularization may be prepared. Such particles may be used to effectively combat and inhibit undesirable ocular neovascularization, edema, or inflammation when surgically implanted into the vitreous of the eye. Such particles may remain in the vitreous to biodegrade after treatment is complete. The preferred amount of fluocinolone acetonide used in these particles ranges from about 0.01 mg to about 15 mg. More preferably, such particles contain from about 0.1 mg to about 6 mg of fluocinolone acetonide. These ranges may provide sustained release of the fluocinolone acetonide for a period of from several hours to many days. Preferred permeable seals in accordance with the present invention are formed of polyvinyl alcohol, which is preferably cross-linked.

EXEMPLIFICATION

Reservoir Manufacture

Figure 5:
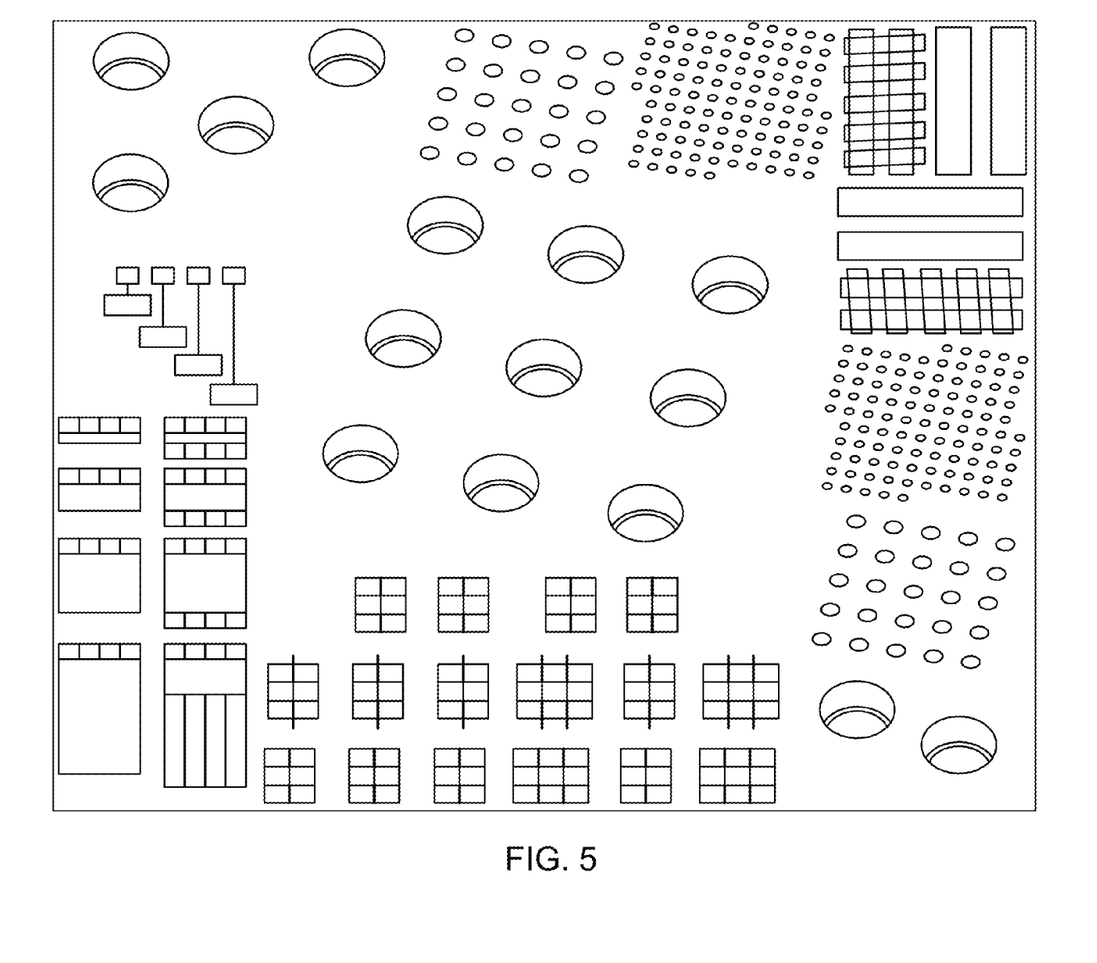
FIG. 5. Wafers of silicon micro-machined to produce wells of varying diameter.

Reservoirs in bulk silicon wafers are manufactured by standard methods known to those skilled in the art of silicon microfabrication in general, and Microelectromechanical systems (MEMS) in particular. Such processing techniques may be found in publications such as VLSI Technology by S.M. Sze pp 676 2nd Edition (McGraw Hill 1988) and An Introduction to Microelectromechanical Systems Engineering pp 265 (Artech House Inc. 2000). FIG. 5 depicts a plate of electronics grade silicon micro-machined to produce wells of varying diameters.

Silicon wafers have diameters in the range of 75-350 mm in diameter, such as 150 mm, 200 mm or 300 mm in diameter. They may be heavily p-type wafers with resistively in the range 0.1-0.001 ohm/cm. Fabrication begins by deposition and photolithographic patterning of an electrically insulating material onto the most polished face of the wafer. This material serves as an etch mask and is typically silicon nitride, silicon oxide or a specific polymer.

A pattern appropriate for creating arrays of cylindrical reservoirs is transferred into the mask material (0.3-0.5 micron thick amorphous silicon nitride deposited by PECVD) by UV photolithography and them etching, in for example, a hydrofluoric acid based solution. The patterned overlay then serves as an etch mask for subsequent etching of exposed silicon. This is carried out using wet or dry etching techniques. An example of a wet etch is concentrated KOH (30-40 wt %) at 80-85° C. Examples of dry etching techniques are Reactive Ion Etching (RIE) or Ion Beam Etching (IBE). Use of these directional etching techniques allow the realization of hundreds to thousands or reservoirs per processed wafers. In a preferred embodiment, a 200 mm diameter wafer of 0.725 mm thickness is processed to yield an array of cylindrical reservoirs of dimensions: 250 micron internal diameter and 725 micron length. The spatial arrangement and spacing of the reservoirs in the wafer is varied to provide sufficient mechanical strength for subsequent dicing of the wafer into single or multiple reservoir particles in particulate form.

Porosification of the Reservoir Walls

The micromachined wafer, in the form of a macroporous membrane, is planarized by impregnation of an electrical insulating and HF-resistant material into the reservoir array. The planarized wafer is then subjected to extended electrochemical etching ("anodisation") in a suitable electrochemical cell, in order to convert the remaining silicon (the reservoir walls) into mesoporous form. This process is well studied and has been reviewed by, for example, Halimaoui in Properties of Porous Silicon pp 405 (IEE 1997 Edited by L. T. Canham). Mesoporous silicon is known to form when silicon is anodically biased in HF-based solutions. Electrolyte flow into the micromachined reservoir volume is prevented by their temporary filling. This forces all current to flow perpendicular to the wafer surfaces, through the remaining silicon.

To porosify right through a patterned wafer will typically require current densities in the range of 5-500 mA/cm$^2$ for periods of 2-5 hours, in electrolytes that contain hydrofluoric acid and a surfactant, the optimum etch conditions depending on the pre-patterning and etched array design of the wafer. Once fully porosified, the planarization agent is removed by a solvent that does not dissolve mesoporous silicon.

Partial Stabilization of the Reservoir Walls

The HF-etched mesoporous membrane has a silicon hydride surface chemistry. This is converted to a silicon oxide surface through a controlled oxidation step. This may be thermal oxidation, such as 500-800° C. in air for periods ranging from 10 minutes to 5 hours such as 700° C. for 30 minutes. It may alternatively be via the use of another oxidizing gaseous ambient or via chemical oxidizing agent such as water, hydrogen peroxide, amines or ozone.

Drug Loading into Reservoirs

The reservoir array can be filled with drug by either conventional pharmaceutical techniques or by newer microtechniques. Examples of the former include methods that exploit capillary forces such as solvent techniques or ink jet printing and microinjection techniques. In the latter case, an array of injectors is designed and aligned to match the reservoir design and ensure massive parallel injection from one nozzle per micromachined reservoir.

Microcapsule Separation

The micromachining process above can include a shallow trench etch step to define and facilitate where the wafer microcapsules are to be broken through controlled fracture into a large number of discrete particles. Alternatively, a wafer can be sawn into microcapsules, e.g., in a standard, high precision, automated dicing machine.

Release Studies

Figure 6:
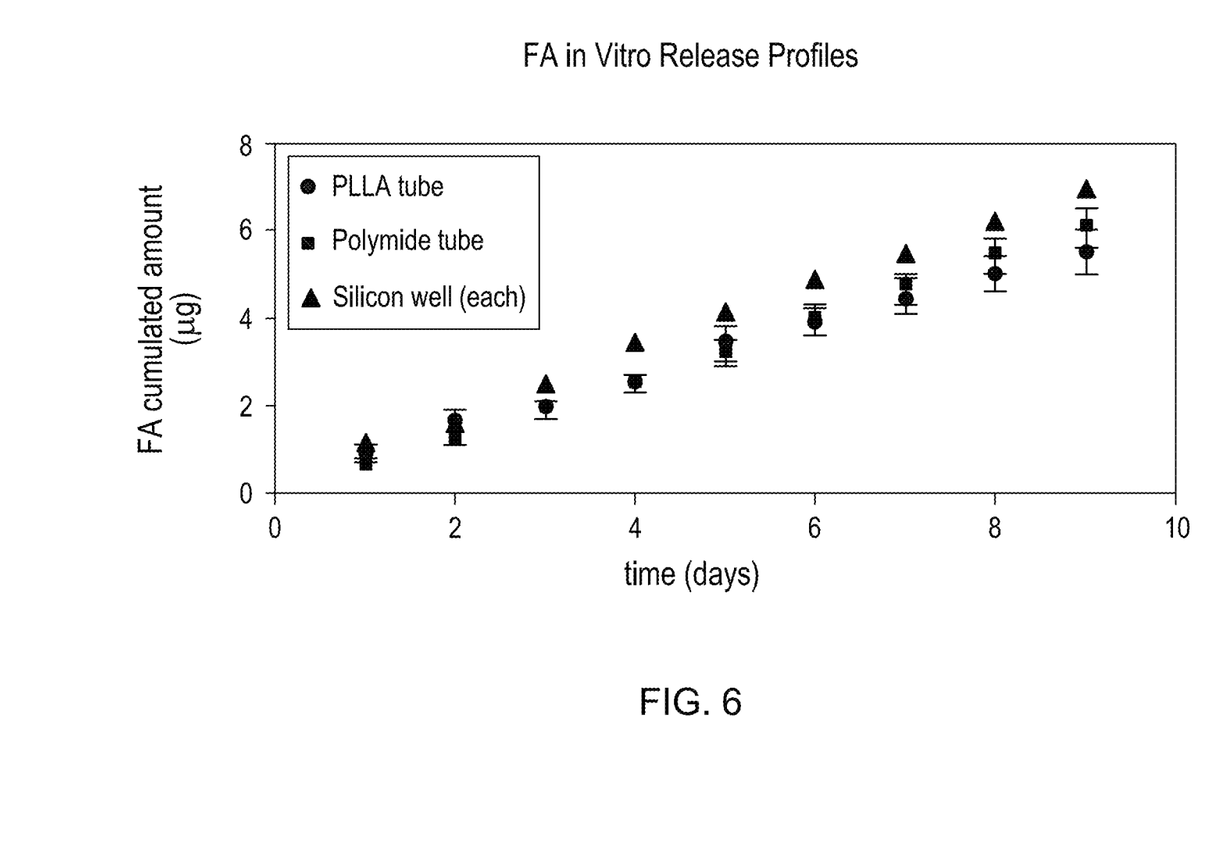
FIG. 6. In vitro release profiles of fluocinolone acetonide (FA)-releasing particles.
Figure 7:
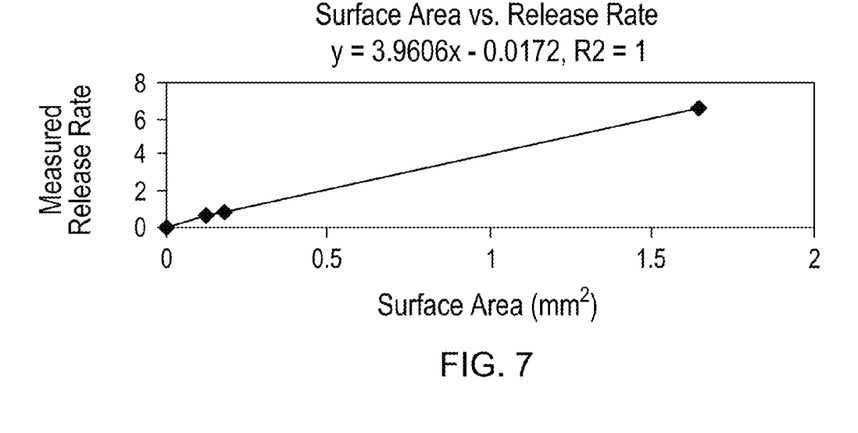
FIG. 7. The release rate per unit surface area of the reservoir.
Figure 8:
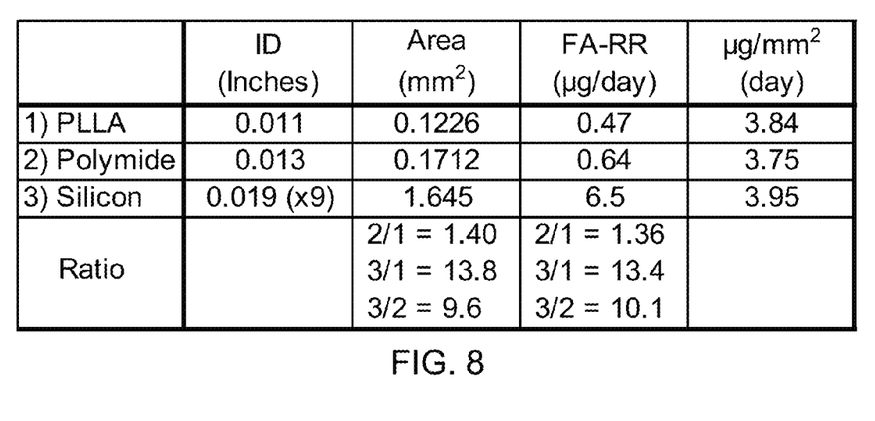
FIG. 8. Comparison of release rates of silicon particles with those from Iluvien style particles made from either a non-erodible (polyimide) tube or a bioerodible (poly-L-lactic acid) form.

Separated arrays were immersed in phosphate buffer (pH 7.4) at 37° C. Samples were taken periodically and replaced with fresh buffer and the drug release rate determined by high performance liquid chromatography (HPLC). Release rates were compared with those from Iluvien style particles made from either a non-degradable tube (poly-imide) or a biodegradable form (poly-L-lactic acid) (FIGS. 6 and 8). The release rate per unit surface area of the diffusion pore was plotted and found to be linear (FIG. 7).

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A biodegradable drug-eluting particle comprising:
a porous silicon body;
a reservoir formed within the porous silicon body having at least one opening to an exterior of the body, wherein the reservoir has a diameter of at least about 120 μm;
a drug core within the reservoir wherein the drug core comprises a therapeutic or diagnostic agent; and
an agent-permeable seal disposed over the at least one opening.

2. The particle of claim 1, wherein the agent-permeable seal provides for sustained release of the agent.

3. The particle of claim 1, wherein the particle has at least two openings to an exterior of the body and an agent-permeable seal disposed over the at least two openings.

4. The particle of claim 3, wherein the particle has a plurality of openings to an exterior of the body and one or more agent-permeable seals covering each of the plurality of openings.

5. The particle of claim 1, wherein the particle has at least one dimension less than 1 mm.

6. The particle of claim 5, wherein the particle has at least one dimension from 20-600 microns.

7. The particle of claim 6, wherein the particle has at least one dimension from 100-500 microns.

8. The particle of claim 1, wherein the porous silicon body is macroporous.

9. The particle of claim 1, wherein the porous silicon body is mesoporous.

10. The particle of claim 1, wherein the porous silicon body is microporous.

11. The particle of claim 1, wherein the porous silicon body is essentially impermeable to the passage of the therapeutic or diagnostic agent.

12. The particle of claim 1, wherein the porous silicon body has a porosity from 20% to 70%.

13. The particle of claim 1, wherein the drug core comprises 0.01 to 50 mg of the agent.

14. The particle of claim 13, wherein the drug core comprises from 0.05 to 20 mg of the agent.

15. The particle of claim 1, wherein the drug core comprises a therapeutic agent.

16. The particle of claim 15, wherein the therapeutic agent is for treating or preventing an ocular condition.

17. The particle of claim 16, wherein the therapeutic agent is fluocinolone acetonide.

18. The particle of claim 1, wherein the drug core comprises a diagnostic agent.

19. The particle of claim 18, wherein the diagnostic agent is for ophthalmic use.

20. The particle of claim 1, wherein the drug core comprises polyvinyl alcohol.

21. The particle of claim 1, wherein the agent-permeable seal comprises polyvinyl alcohol.

22. The particle of claim 1, wherein the particle is partially biodegradable in a patient.

23. The particle of claim 1, wherein the particle is completely biodegradable in a patient.

24. The particle of claim 1, wherein the particle has a lifespan of about 1 month.

25. The particle of claim 1, wherein the particle has a lifespan of about 1 year.

26. The particle of claim 1, wherein the reservoir has a diameter of about 120 µm to about 300 µm.

27. A method for treating a patient to obtain a desired local or systemic physiological or pharmacological effect comprising administering the biodegradable drug-eluting particle of claim 1 to a patient and allowing the agent to elute from the particle and come in direct contact with cells or tissues of the patient.

28. The method of claim 27, comprising administering a plurality of particles in a single administration.

29. The method of claim 27, wherein the particle is administered intraocularly.

30. A method for manufacturing biodegradable porous silicon particles, comprising:
providing a silicon wafer,
depositing and patterning a material on the wafer for use as an etch mask,
etching a plurality of reservoirs in the wafer, wherein each reservoir has a diameter of at least about 120 µm,
introducing pores into the silicon substrate,
filling the reservoirs with a drug core comprising a therapeutic or diagnostic agent, and
covering the reservoirs with one or more agent permeable seals.

31. The method of claim 30, wherein etching a plurality of reservoirs in the wafer is performed prior to introducing pores into the silicon wafer.

32. The method of claim 30, wherein introducing pores into the silicon wafer is performed prior to etching a plurality of reservoirs in the wafer.

33. The method of claim 30, wherein the agent-permeable seal comprises a polymer.

34. The method of claim 30, wherein the method further comprises subdividing the wafer through controlled partitioning into a number of discrete particles.

* * * * *